United States Patent [19]

Snyder et al.

[11] 4,432,749
[45] Feb. 21, 1984

[54] SELF-CONTAINED SWAB UNIT

[75] Inventors: Thomas A. Snyder, Willow Grove; Walter T. Leible, Warminster, both of Pa.

[73] Assignee: Hillwood Corporation, Warminster, Pa.

[21] Appl. No.: 360,038

[22] Filed: Mar. 19, 1982

Related U.S. Application Data

[63] Continuation-in-part of Ser. No. 135,412, Mar. 31, 1980, abandoned.

[51] Int. Cl.³ .......................................... A61M 35/00
[52] U.S. Cl. ........................................ 604/2; 401/185
[58] Field of Search ................... 604/1, 2, 3; 401/132, 401/139, 183, 185, 186, 196, 205, 206, 264, 273, 272; 222/632, 633, 636, 209

[56] References Cited

U.S. PATENT DOCUMENTS

| | | |
|---|---|---|
| 3,495,917 | 2/1970 | Truhan . |
| 3,759,259 | 9/1973 | Truhan . |
| 3,876,314 | 4/1975 | Nehring . |
| 3,890,954 | 6/1975 | Greenspan . |
| 3,938,898 | 2/1976 | Reitknecht . |
| 4,014,746 | 3/1977 | Greenspan . |
| 4,133,614 | 1/1979 | Baginski et al. . |
| 4,150,904 | 4/1979 | Stewart . |
| 4,173,978 | 11/1979 | Brown . |

FOREIGN PATENT DOCUMENTS

| | | | |
|---|---|---|---|
| 500381 | 2/1939 | United Kingdom | ..................... 604/1 |
| 1060288 | 3/1967 | United Kingdom . | |
| 1164877 | 9/1969 | United Kingdom . | |
| 1170341 | 11/1969 | United Kingdom . | |
| 1175249 | 12/1969 | United Kingdom . | |

Primary Examiner—C. Fred Rosenbaum
Assistant Examiner—T. J. Wallen
Attorney, Agent, or Firm—Panitch, Schwarze, Jacobs & Nadel

[57] ABSTRACT

A self-contained swab unit comprises a cylindrical plastic tube having a foam rubber swab capping one end. The tube is closed at the opposite end by a heating and crimping process. A cleansing or sterilizing solution is loaded into the tube. The tube is sealed by a plug having a diameter slightly larger than the inside diameter of the cylinder, so that the solution is sealed away from the foam rubber swab when not in use. Squeezing the tube causes the plug to pivot in relation to the wall of the tube so that the seal is broken and liquid may saturate the swab. Releasing the squeeze pressure on the tube causes the plug to pivot back into a partial seal so that the amount of fluid used in swabbing can be controlled.

5 Claims, 3 Drawing Figures

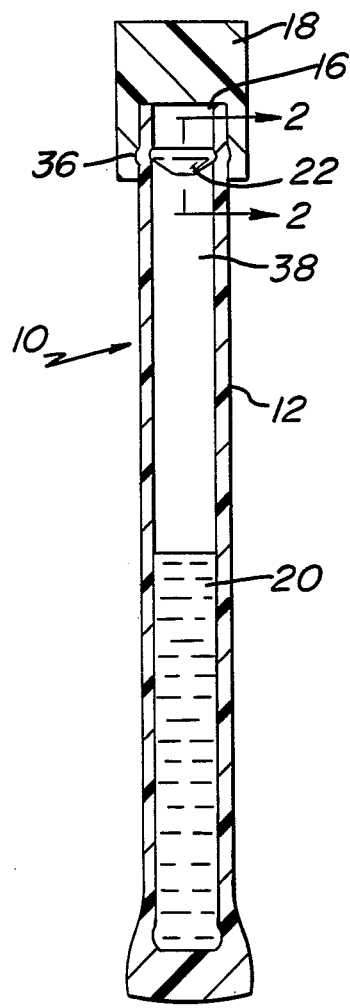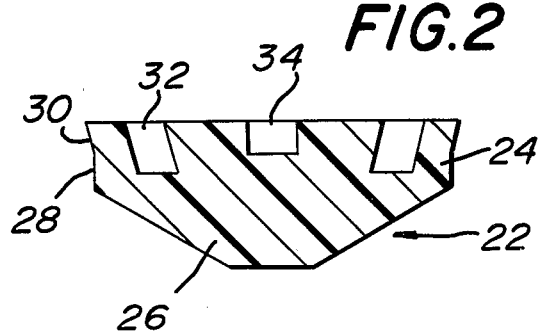

SELF-CONTAINED SWAB UNIT

CROSS-REFERENCES TO RELATED APPLICATIONS

This application is a continuation-in-part of copending application Ser. No. 135,412, filed Mar. 31, 1980, now abandoned.

This invention is related to our U.S. patent application for a "Disposable Swab and Culture Unit", Ser. No. 135,422, filed Mar. 31, 1980, now U.S. Pat. No. 4,312,950, issued Jan. 26, 1982. Said patent is incorporated herein by reference.

BACKGROUND OF THE INVENTION

A self-contained disposable swab is a useful device, particularly for medical applications. Prior to such self-contained devices, the various swabbing solutions, such as germicidal soap, detergents, and medications were stored in capped bottles containing much more solution than would normally be necessary for a single use. Dry absorbent swabs, such as the common cotton swab on a wood stick were kept in separate body. The user normally selected one such swab and dipped it into the swabbing solution appropriate for the task. There were several inconveniences associated with this older method. The primary inconvenience was the necessity of carrying along relatively large bottles of the various solutions in doctor's bags or first-aid kits. Additionally, where the swab would be placed in contact with contaminants or bacteria, the swab could not be re-dipped into the bottle to get more solution. Instead, a new swab had to be used each time it was necessary to wet the swab tip.

Self-contained swab units have proven to be a convenient solution to the above-mentioned problems. Each unit carries an amount of solution judged to be approximately right for one usage. The solution is sealed away from the swab when not in use so that the unit may be stored and carried in a doctor's bag or in a technician's portable kit until it is needed. The unit, exclusive of the solution, is relatively inexpensive and thus is suitable for disposable use.

OBJECT OF THE INVENTION

An object of the present invention is to provide an improved self-contained swab unit of the type described above. Specifically, it is desired to provide an improved means of maintaining a rupturable seal between the swab and the liquid. Ideally, such a seal would be airtight and watertight even when the unit is subjected to minor blows, such as would occur in a doctor's bag or technician's kit, and when placed under a modest weight such as other medical instruments being stored upon it. Yet the seal should be easily openable when the swab is to be used. Additionally, it would be an advantageous feature if the seal would be partially closeable on demand so that the flow of the liquid to the swab could be regulated.

Since the units are intended to be disposable, the cost factor is important. The seal that meets the operational requirements of the previous paragraph must also be capable of being installed in the unit inexpensively. This will almost invariably necessitate that the seal be installed by a simple automated process. It is toward these dual objects, an improved seal at a reasonable cost that the present invention is directed.

SUMMARY OF THE INVENTION

A disposable self-contained swab unit is made in the form of a generally hollow container, such as a cylinder, having a closed end and an open end capped by a swabbing structure. A liquid medium is held within the container. The swabbing structure can be a foam rubber cube mounted over and encompassing the open end of the container. A plug having a body is disposed within the container such that the bottom of the body is juxtaposed to the liquid medium and the top of the body is juxtaposed to the swabbing means. The top of the body of the plug has a diameter larger than the bore diameter of the container. The body of the plug is tapered inwardly from the top of the body towards the bottom of the body. This body has an annular chamber disposed radially inwardly from said taper so as to facilitate inward deformation of the tapered surface. The plug is inserted within the bore of the container to form a sealed compartment for holding the liquid medium in that portion of the container between the closed end and the plug. In use, the tube is squeezed causing the plug to move relative to the walls of the container allowing the liquid medium to flow past the plug to contact the swabbing structure. The unit is then used as swab with the container forming a handle.

When the squeeze on the tube is released, the plug moves back to approximately its original position relative to the walls of the container effecting a partial seal, and thus regulating flow of the liquid medium to the swabbing structure.

For the purpose of illustrating the invention, there is shown in the drawings a form which is presently preferred; it being understood, however, that this invention is not limited to the precise arrangements and instrumentalities shown.

BRIEF DESCRIPTION OF THE DRAWING

FIG. 1 is a longitudinal section view of a swab unit according to the present invention.

FIG. 2 is a cross-sectional view of the plug taken along line 2—2 of FIG. 1.

FIG. 3 is a bottom view of the plug.

DETAILED DESCRIPTION OF THE DISCLOSURE

Referring to the drawing in detail, wherein like numerals indicate like elements, the present invention is embodied in a disposable self-contained swab unit designated generally as 10. The unit 10 includes a cylindrical plastic tube 12 closed at one end 14 and open at the other end 16. Tube 12 is preferably made of plastic such as polypropylene or a copolymer blend selected to preserve the integrity of the seal chamber.

A foam rubber cube 18 caps the open end of tube 16. Cube 18 is herein shown as a foam rubber cube, but it will be understood that any suitable absorbent material may be used and any convenient geometric configuration may be employed, as the function of cube 18 is to absorb the swabbing solution and apply it to the area being swabbed. Cube 18 is attached to tube 12 by a suitable glue or adhesive.

A liquid solution 20 is loaded to a predetermined amount in tube 12. The solution can be a liquid detergent, a germicidal soap, a medication or any of a variety of other liquids normaly applied with a swab. When tube 12 is constructed of a transparent plastic, the liquid will be visible through the wall of tube 12. It may therefore be advantageous to use appropriate dyes to color code the various liquids in different swab units so that ready identification is available. Also, printing may be applied to the tube to identify the contents of the tube and/or instructions for use.

The liquid 20 is sealed away from cube 18 by plug 22. Plug 22 may be best viewed in FIG. 2. Plug 22 has a top body portion 24 and a bottom body cone portion 26. The top body portion 24 has a cylindrical surface defined along its outside diameter by straight section 28 and tapered section 30. Tapered section 30 has a larger outside diameter than straight section 28. Annular chamber 32 in the top body portion 24 facilitates the tapered section 30 to act as a ring or flange.

A centering depression 34, shown as a rectangular depression in these drawings, is provided so that a centering tool may be used to place the plug 22 within the tube. The plug 22 is preferably a plastic material integrally formed by injection molding.

The outside diameter of the top body portion 24 of plug 22 is slightly larger than the inside diameter of tube 12. Tube 12 is preferably composed of a sufficiently pliable material such as polypropylene or a copolymer blend. In this manner, the wall of tube 12 will bulge outwardly as shown at 36 to accommodate the top body portion 24 of plug 22, thus causing a sealed cavity 38 in tube 12 which will serve as a reservoir for the liquid 20.

When the plug 22 is inserted in tube 12, the straight section 28 of the plug 22 creates an outward pressure that forces upon the side wall of the tube 12, causing the tube 12 to distort, and create a seal. Secondly, the tapered section 30 (flange ring section) of the plug 22 will take on outside dimensions that will equal the internal dimension of the tube 12. As the product ages, the elasticity of the tube 12 may change and the force applied to the sidewall may change the internal dimensions of the tube 12. When this occurs, the flange 30 will move and seat itself against the wall of the tube 12, preventing a weak spot or gap from occurring, thus preventing a possible leak.

Self life studies showed evidence of leakage at varying degrees of time and at a percentage level (approximately 15%) that might be unacceptable for various liquids occurring around a plug similar to that depicted in FIG. 2, but without a flange. In view of this, applicants employed an additional feature in order to make a part of the plug 22 flexible so that it would provide a free form lip or section that would maintain the seal condition for the life of the product.

Accordingly, the tapered section 30 relies on the flange (live hinge) to form a seal with the tube 22. The seal is effectuated by the elasticity of the flange. The primary seal, however, is provided by the straight section 28 which relies on a deformation of the elasticity of the wall of the tube 12 to form a seal by insertion of a plug which has a larger diameter than the bore of the cylinder.

The plug 22 of this invention thus provides two sealing mechanisms. The flange 30 takes advantage of is own flexibility to form a seal, while the straight section 28 relies on the flexibility of the tube 12. The flange section 30 also prevents leakage via capillary action of the liquid 20. The annular chamber 32 in the plug 22 which forms the flange 30 provides pliability to the flange 30.

In one particular embodiment, the top body portion 24 of plug 22 has a diameter of about 0.32 inches with the lengths of the straight section 28 and the tapered section each being about 0.025 inches. In this embodiment, the taper is at an angle of about 15° from the vertical and the side wall of the bottom body cone portion 26 is at an angle of about 30° from the horizontal.

In construction and assembly of the device 10, tube 12 is loaded to a pre-determined amount with liquid 20. Plug 22 is then inserted into the open end 16 of tube 12, with the bottom body section 26 of plug 22 entering open end 16 first. A centering tool (not shown) is used in cooperation with centering depression 34 to position and center plug 22 in tube 12. A suitable glue or adhesive is then applied either to the cavity in cube 18 or to the upper extremity of tube 12, and cube 18 is seated as a cap over tube 12. The glue, or adhesive, when dry, holds cube 18 in place.

The swabbing unit 10 is then ready for storage. In this position, the liquid 20 is sealed against contamination or evaporation. The foam rubber cube 18 is dry. The unit 10 can be stored in any position without having the liquid 20 saturate cube 18. The unit 10 can even withstand moderate jolts and weights without having the seal ruptured.

Immediately prior to use, the unit 10 is inverted so that cube 18 points downward, and tube 12 is squeezed between the thumb and forefinger. The pressure of fluid 20 on the bottom body portion 26 causes plug 22 to pivot relative to the walls of tube 12. Liquid 20 then flows past plug 22 and saturates cube 18. When the user releases the squeezing pressure on tube 12, suction in tube 12 will pivot plug 22 back towards its sealing position. While the force of the suction will not be great enough to completely center and align plug 22 to its original position, it will cause straight section 28 and tapered section 30 of plug 12 to contact the inside wall of tube 12, thus effecting a partial seal. This allows the user to control the rate at which he uses fluid 20.

It can thus be seen that the objects of the invention have been accomplished, i.e., providing a self-contained swab unit having an improved seal at a reasonable cost.

The present invention may be embodied in other specific forms without departing from the spirit or essential attributes thereof and, accordingly, reference should be made to the appended claims, rather than to the foregoing specification, as indicating the scope of the invention.

We claim:
1. A disposable swab unit comprising:
(a) a generally hollow container adapted to be squeezed, said container having a wall, a closed end and an open end capped by a structure providing a swabbing means;
(b) a liquid medium within the hollow container;
(c) a plug having a body, the bottom of said body juxtaposed to said liquid medium and the top of said body juxtaposed to said swabbing means, the top of said body having a diameter larger than the inner diameter of the container, said body being tapered inwardly from the top of said body towards the bottom of said body, said body having an annular chamber disposed within the top surface thereof radially inwardly from said taper to facilitate inward deformation of said tapered surface, the plug inserted within said container to form a sealed compartment for holding the liquid medium in the portion of said container between the closed end and the plug said plug being pivotable relative to the container wall so as to allow said liquid medium to flow past said plug to contact said swabbing means upon squeezing of said container.

2. A disposable swab unit as in claim 1 wherein said container is a cylindrical tube.

3. A disposable swab unit as in claim 2, wherein the closed end of said tube is formed by a heating and crimping process.

4. A disposable swab unit as in claim 2, wherein said tube is made of a plastic material.

5. A disposable swab unit as in claim 1 or 2 wherein the swabbing structure is a foam rubber cube mounted over and encompassing the open end of the container.

* * * * *